US011006932B2

(12) United States Patent
Hoelscher et al.

(10) Patent No.: US 11,006,932 B2
(45) Date of Patent: May 18, 2021

(54) METHODS AND DEVICES FOR DIAGNOSIS OF BLOOD VESSEL BLOCKAGE OR HEMORRHAGE

(71) Applicant: The Regents of the University of California, Oakland, CA (US)

(72) Inventors: Thilo Hoelscher, San Diego, CA (US); Arne Voie, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 505 days.

(21) Appl. No.: 14/776,664

(22) PCT Filed: Mar. 14, 2014

(86) PCT No.: PCT/US2014/028468
§ 371 (c)(1),
(2) Date: Sep. 14, 2015

(87) PCT Pub. No.: WO2014/144171
PCT Pub. Date: Sep. 18, 2014

(65) Prior Publication Data
US 2016/0030009 A1    Feb. 4, 2016

Related U.S. Application Data

(60) Provisional application No. 61/799,199, filed on Mar. 15, 2013.

(51) Int. Cl.
A61B 8/00    (2006.01)
A61B 8/08    (2006.01)

(52) U.S. Cl.
CPC .............. *A61B 8/56* (2013.01); *A61B 8/0808* (2013.01); *A61B 8/0891* (2013.01);
(Continued)

(58) Field of Classification Search
None
See application file for complete search history.

(56) References Cited

U.S. PATENT DOCUMENTS 5,724,976 A    3/1998   Mine et al.
6,132,379 A    10/2000   Patacsil et al.
(Continued)

OTHER PUBLICATIONS

Sarkar et al., "Role of transcranial Doppler ultrasonography in stroke". Postgrad Med. J. 2007; 83:683-689.*
(Continued)

*Primary Examiner* — Pascal M Bui Pho
*Assistant Examiner* — Yi-Shan Yang
(74) *Attorney, Agent, or Firm* — Mayer & Williams; Stuart H. Mayer

(57) ABSTRACT

A method of diagnosing the occurrence or non-occurrence of a blood vessel blockage or hemorrhage comprises non-invasively applying ultrasound to a location on a patient's body, where the ultrasound is applied in an alternating and pulsed fashion, administering acoustic amplifiers to the patient, monitoring a feedback acoustic response signal of the acoustic amplifiers triggered by the ultrasound, and determining a diagnosis based at least in part on a relationship between an acoustic response signature of the acoustic response signal and a baseline acoustic response signature.

18 Claims, 8 Drawing Sheets

(52) U.S. Cl.
CPC ............ *A61B 8/4477* (2013.01); *A61B 8/481* (2013.01); *A61B 8/5223* (2013.01)

(56) References Cited

U.S. PATENT DOCUMENTS

| | | | | |
|---|---|---|---|---|
| 6,945,937 | B2* | 9/2005 | Culp | A61B 17/22004 600/437 |
| 7,037,267 | B1* | 5/2006 | Lipson | A61B 5/6834 600/437 |
| 8,038,622 | B2 | 10/2011 | Abraham | |
| 2002/0065467 | A1* | 5/2002 | Schutt | A61B 5/055 600/454 |
| 2002/0107473 | A1* | 8/2002 | Bond | A61B 17/22004 604/22 |
| 2002/0198469 | A1* | 12/2002 | Bridger | A61B 5/4818 600/586 |
| 2004/0138563 | A1* | 7/2004 | Moehring | A61B 8/06 600/439 |
| 2007/0016041 | A1* | 1/2007 | Nita | A61N 7/022 600/439 |
| 2007/0167705 | A1* | 7/2007 | Chiang | A61B 5/6805 600/407 |
| 2009/0036780 | A1* | 2/2009 | Abraham | A61B 8/08 600/459 |
| 2011/0178441 | A1* | 7/2011 | Tyler | A61N 7/00 601/2 |
| 2011/0263983 | A1* | 10/2011 | Peszynski | A61B 1/0052 600/443 |
| 2012/0165670 | A1* | 6/2012 | Shi | A61B 8/481 600/442 |
| 2013/0072907 | A1 | 3/2013 | Lichty, II et al. | |
| 2013/0261461 | A1* | 10/2013 | Murakami | A61B 8/0883 600/443 |

OTHER PUBLICATIONS

Krejza et al., "Transcranial Color Doppler Sonography of Basal Cerebral Arteries in 182 Healthy Subjects: Age and Sex Variability and Normal Reference Values for Blood Flow Parameters", AJR 1999; 172:213-218.*

Meyer-Wiethe et al., "Diagnosis of intracerebral hemorrhage with transcranial ultrasound". Cerebrovasc. Dis. 2009; 27(Suppl 2): 40-47.*

Zanette et al., "Comparison of Cerebral Angiography and Transcranial Doppler Sonography in Acute Stroke". Stroke, 1989;20:899-903.*

Alexandrov et al., "Intracranial Blood Flow Velocities in Acute Ischemic Stroke". Stroke, 1994; 25:1378-1383.*

Maurer et al., "Differentiation between intracerebral hemorrhage and ischemic sroke by transcranial color-coded duplex sonography". Stroke, 1998;29:2563-2567.*

Sirsi et al., "Microbubble compositions, properties and biomedical applications". Bubble Sci Eng Technol. 2009; 1:3-17. (Year: 2009).*

Epstein et al., "On the stability of gas bubbles in liquid-gas solutions". The Journal of Chemical Physics, 1950, vol. 18, No. 11, pp. 1505-1509. (Year: 1950).*

International Preliminary Report on Patentability dated Sep. 15, 2015 in connection with corresponding International Application No. PCT/US2014/028468 (8 pages total).

* cited by examiner

Table: Output Power Presets $PS_{m,n}$

| Age (years) | Caucasian (m=1:3) | | Hispanic (m=4:6) | | Asian (m=7:9) | | African-American (m=10:12) | |
|---|---|---|---|---|---|---|---|---|
| | female | male | female | male | female | male | female | male |
| <45 | $PS_{1,1}$ | $PS_{1,2}$ | $PS_{4,1}$ | $PS_{4,2}$ | $PS_{7,1}$ | $PS_{7,2}$ | $PS_{10,1}$ | $PS_{10,2}$ |
| 45-65 | $PS_{2,1}$ | $PS_{2,2}$ | $PS_{5,1}$ | $PS_{5,2}$ | $PS_{8,1}$ | $PS_{8,2}$ | $PS_{11,1}$ | $PS_{11,2}$ |
| >65 | $PS_{3,1}$ | $PS_{3,2}$ | $PS_{6,1}$ | $PS_{6,2}$ | $PS_{9,1}$ | $PS_{9,2}$ | $PS_{12,1}$ | $PS_{12,2}$ |

$PS_{m,n}$: Output power presets ($PS_{m,n}$), adjusted for gender (female: n=1, male: n=2), age and ethnicity

*FIG. 8*

METHODS AND DEVICES FOR DIAGNOSIS OF BLOOD VESSEL BLOCKAGE OR HEMORRHAGE

This invention was made with government support under HL091043 awarded by the National Institute of Health. The government has certain rights in the invention.

TECHNICAL FIELD

The methods and devices described herein relate to diagnosing the occurrence of a blood vessel blockage or hemorrhage, and in particular, to providing a method and apparatus for diagnosing the underlying cause of stroke by applying ultrasound in combination with intravenously administered acoustic amplifiers through an intact skull.

BACKGROUND

Stroke is the second leading cause of death worldwide and the third leading cause of death in the United States, between cardiac diseases (the number one worldwide common cause of death) and tumor diseases (the number three worldwide common cause of death). Neuronal brain cells (neurons) are very sensitive to oxygen supply, which may be interrupted, for example, due to a sudden arterial vessel occlusion. As a result, neurons turn into apoptosis within the first 60 seconds of oxygen deprivation. Apoptosis is defined as a programmed cell death, which means that neurons start to die irreversibly already at this very early point in time if recanalization, and therefore providing an oxygen supply, does not occur.

In the case of acute ischemic stroke, it has been shown that an average of 1,900,000 neurons die every minute due to intracranial arterial vessel occlusion. Hence, it is a worldwide, common understanding that therapeutic options to recanalize the affected brain artery should be applied as early as possible. Recent advances in stroke care, such as the installation of specialized Stroke Centers/Units or TeleMedicine concepts, have improved stroke care in selected areas. However, all of these activities are either initiated or coordinated mainly by well known academic centers in developed countries, and the overall impact of these improvements on stroke care are negligible. The cause of the worldwide growing incidence of stroke may be attributed to 3 main causes. First, there is a lack of public awareness of the disease and its symptoms. Second, all conventional therapeutic interventions require hospitalization of the patient. Third, and among people of all ages, more than 85% of global deaths from stroke occur in either low or middle-income countries, where approximately 85% of the world's total population resides, as illustrated in FIG. 1.

Currently, tissue Plasminogen Activator, abbreviated tPA, is the worldwide accepted first choice therapeutic intervention in case of acute ischemic stroke. Globally, only about 3% of all stroke victims receive tPA. In the U.S., tPA is the only drug for acute stroke treatment approved by the Food and Drug Administration (FDA). One of the major limitations why only a very limited amount of stroke victims are eligible for tPA therapy is the limited treatment window of 4.5 hours after initial onset of clinical stroke symptoms. If this treatment window is exceeded, tPA will typically not be administered, due to a significant higher risk of harmful events caused by the drug itself. The vast majority of tPA treatment delays are caused by either failure to recognize stroke like symptoms in time and/or delayed transport times to the appropriate hospital where tPA therapy can be provided. Therefore, the diagnosis of ischemic vs. hemorrhagic stroke at the earliest time point possible, means having the capability to do so either at the site of the emergency or during patient transport in ambulances and helicopters, would potentially contribute to a higher referral rate of tPA candidate patients or patients who might benefit from neuro-intervention. The time delay between a '911' call, arrival at the site of the emergency, recognition/interpretation of stroke symptoms and their cause, and transport to the appropriate hospital are limiting factors determining whether a patient survives, suffers from lifelong invalidity or fully recovers without deficits.

SUMMARY

Various embodiments described herein are directed to methods and devices for diagnosis, in the field, during the transport of a patient to the hospital or at any other location, of whether a blood vessel blockage, a hemorrhage or a stroke has occurred, as well as identifying an underlying cause. Such methods and devices may provide the capability to automatically adjust to the individual diagnostic window of respective patients. Methods and devices according to embodiments may employ ultrasound in combination with intravenously administered acoustic amplifiers such as, for example, ultrasound microbubbles, liposomes or acoustic spheres, in the triggering and analysis of acoustic response signals (e.g., stable cavitation), as an underlying mechanism for the differential diagnosis of stroke. Additionally, embodiments described herein can be made to fit in a pocket, be battery operated for ease of transport, or integrated into another ultrasound device or other diagnostic or monitoring device.

BRIEF DESCRIPTION OF THE DRAWINGS

For a more complete understanding of example embodiments described herein, reference is now made to the following descriptions taken in connection with the accompanying drawings in which:

FIG. 8 is a Table showing an array of preset power settings based on race, age and gender of a patient;

DETAILED DESCRIPTION

Methods and apparatus are provided to diagnose patients who may suffer from a blood vessel blockage, a hemorrhage or a stroke, such as an acute ischemic or hemorrhagic stroke. Embodiments may be directed to the non-invasive application of ultrasound in combination with intravenously administered acoustic amplifiers through an intact skull and to trigger an acoustic response (e.g., stable cavitation, inertial cavitation, sub-harmonics, ultra-harmonics, elevation of noise floor) of the acoustic amplifier which could be used to identify occurrence of a stroke and/or differentiate between a primary ischemic or a primary hemorrhagic event as the underlying cause of acute stroke syndrome. Methods and devices in accordance with embodiments are not necessarily based on or do not necessarily employ diagnostic imaging.

Figure 1:
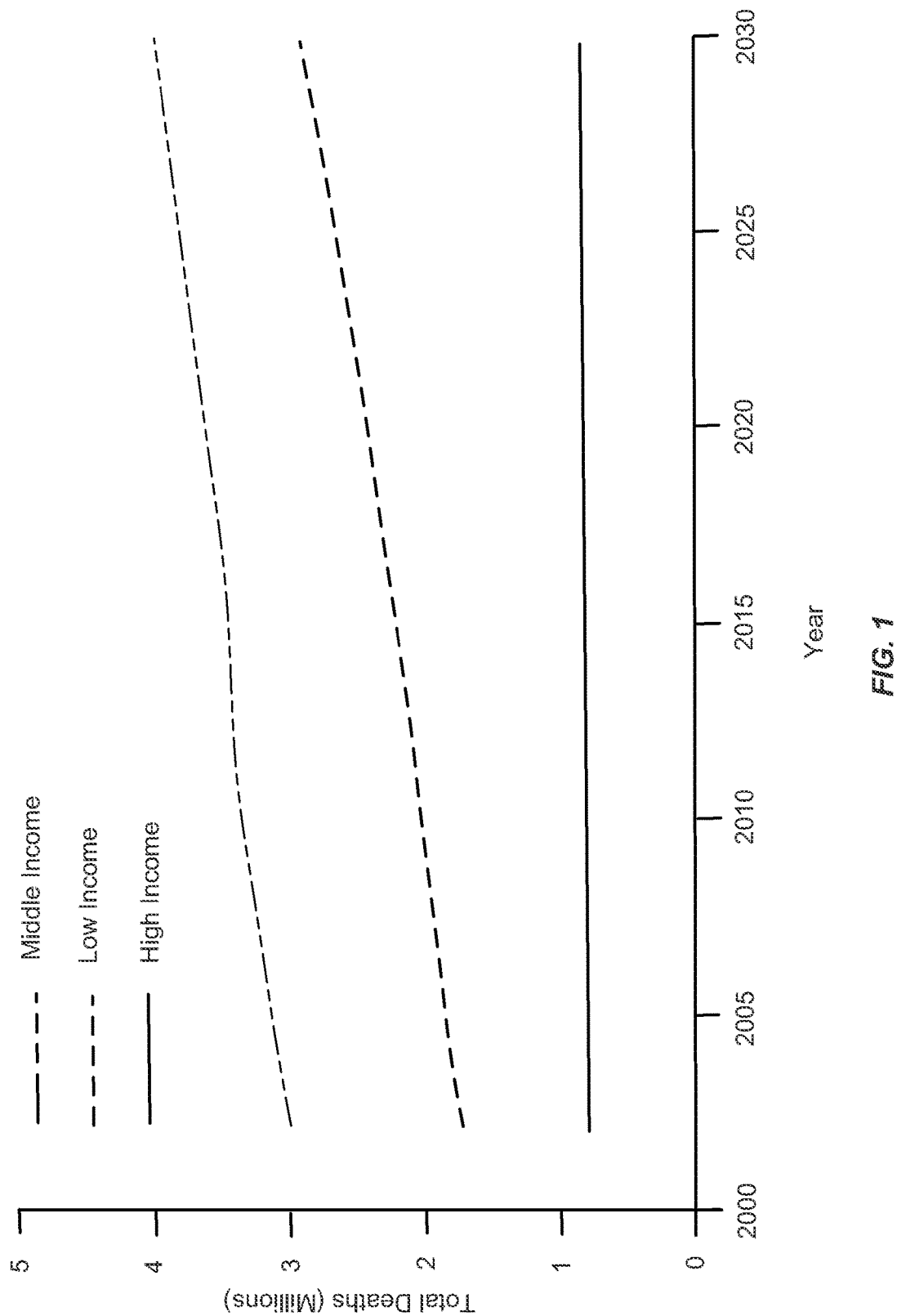
FIG. 1 is a graph illustrating the prevalence of stroke-related deaths among different socio-economic groups.
Figure 2:
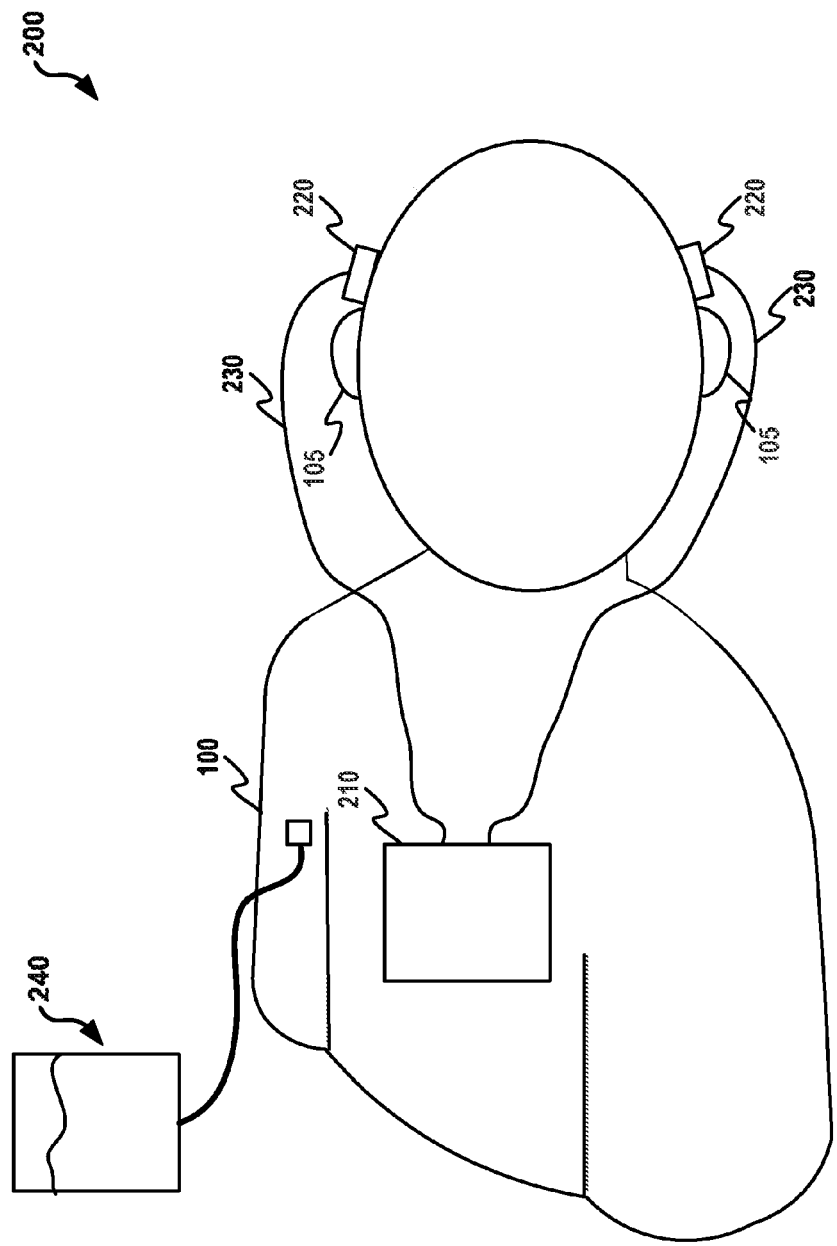
FIG. 2 illustrates an example of a stroke diagnosis system configured and utilized in accordance with various embodiments for treatment of a stroke victim.

FIG. 2 illustrates an example of a stroke diagnosis system configured and utilized in accordance with various embodiments for treatment of a stroke victim 100. A PCM device 210 is electrically coupled, via two transducer cables 230, to two transducers, not shown, included in two ultrasound probes 220 that are non-invasively attached to the stroke victim 100. An intravenous infusion device 240 may be used to administer a microbubble, or other acoustic amplifier, agent to the stroke victim 100.

Ultrasound may be applied to the stroke victim 100 in a pulsed fashion using a transmit frequency between about 100 KHz to about 1000 KHz (for example, about 200 KHz at which distortion of an ultrasound beam by the skull is negligible). The ultrasound may be applied from multiple sides of the head in an alternating fashion to increase the diagnostic area of interest and to avoid, in parallel, potential side effects, due to the overlay of the individual sound fields. The ultrasound probes 220 may be placed in an anatomical area of the temporal bone and close to each ear 105. The ultrasound probes 220 may be reusable or disposable and may have the capability to transmit an ultrasound beam as well as receive acoustic signals, caused by ultrasound acoustic amplifier induced acoustic events, in an alternating fashion. The pulse width may be short (e.g., 10 µs-1000 µs) in combination with a duty cycle between 1-50%. The acoustic output power may be chosen to accomplish a focal maximum intensity below the Food and Drug Administration's (FDA) limit of 720 mWatts/cm$^2$. Methods described herein may be used in combination with acoustic amplifiers such as, for example, ultrasound microbubbles, liposomes or acoustic spheres. Further, methods described herein may be applied short-term, for the purpose of initial diagnosis, or continuously over an extended period of time (e.g., several hours), for the purpose of event monitoring (e.g., potential vessel recanalization due to sonothrombolysis).

Figure 3:
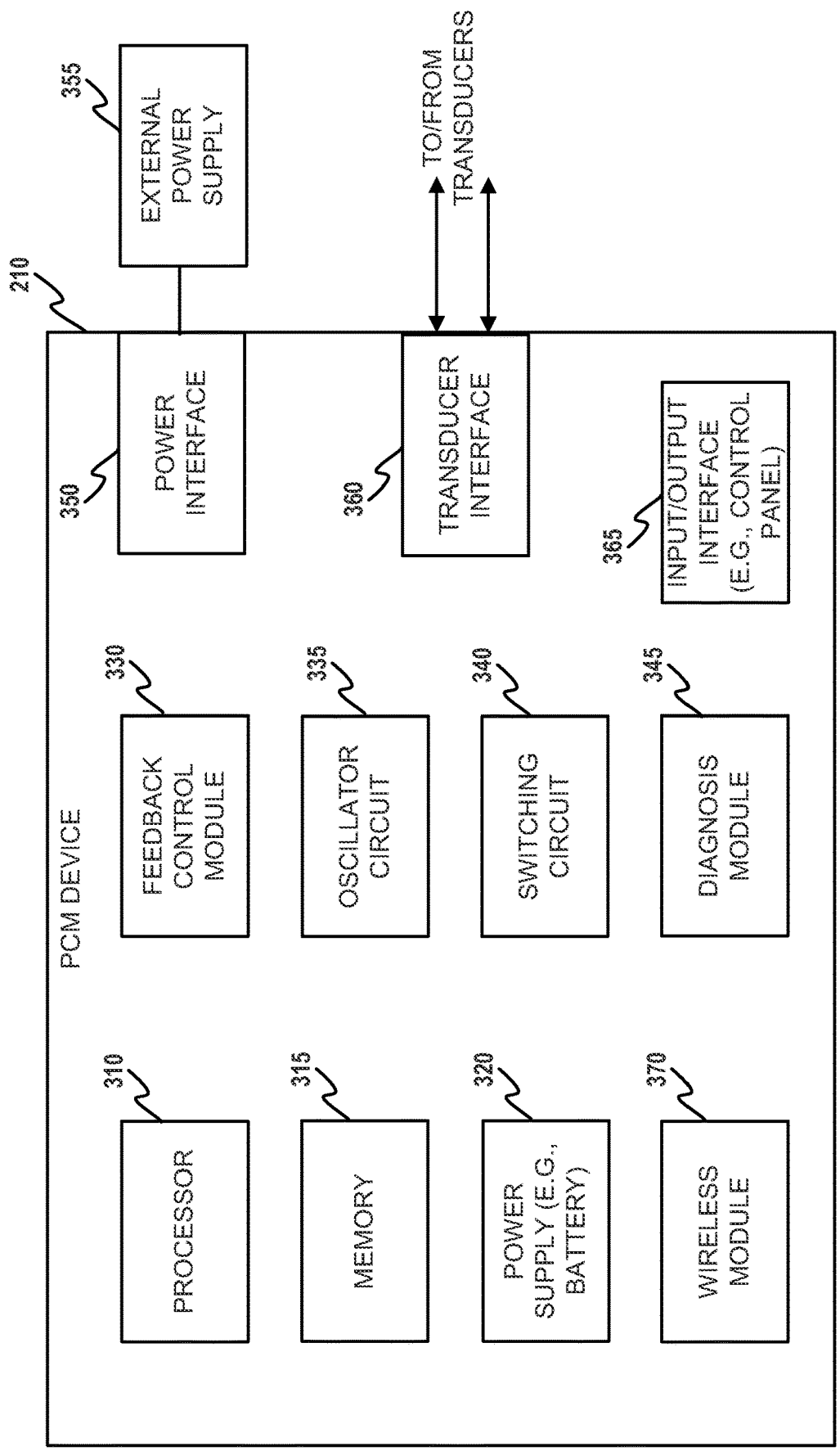
FIG. 3 illustrates a block diagram of an example device configured and utilized in accordance with various embodiments for treatment of a stroke victim.

FIG. 3 illustrates a block diagram of an example of the PCM device 210 configured and utilized for treatment of a stroke victim. The PCM device 210 includes a processor 310, a memory 315, a power supply (e.g., a battery) 320, a feedback control module 330, an oscillator circuit 335, a switching circuit 340, a diagnosis module 345, a power interface 350, a transducer interface 350, an input/output (I/O) interface (e.g., a control panel) 365 and a wireless communication module 370.

In various examples, the memory 315 may be a non-transitory memory device. In various examples, the memory 315 may be integrally formed with the processor 310 or may be an external memory device. The memory device 315 may include program code that may be executed by the processor 310. For example, the program code may cause the processor 310 to execute functions of one or more modules to execute processes as described below In an embodiment, the PCM device 210 may be small, preferably pocket sized. In this embodiment, the PCM device 210 may be powered by the power supply 320 to provide portable and wireless use. The power supply 320 may be charged by an external power supply 355 via the power interface 350. In this embodiment, the PCM may be approximately the size of a hand-held digital multimeter, or around 2 inches by 4 inches by 8 inches. Most of the volume and weight of the PCM may be due to the battery. The PCM battery may be rechargeable, may have the capacity to be operated directly from a wall outlet, and may be easy to replace with a charged battery for extended use away from other power sources. In another embodiment, the PCM device 210 may be a stationary, or mostly stationary device or an integrated part of another ultrasound, diagnostic, or monitoring device, and receive power from the external power supply 355 and/or the power supply 320.

The feedback control module 330 receives acoustic feedback signals from the transducer probes 220 and controls the output power of the oscillator circuit 335 to achieve a safe steady state power level that provides an acoustic response signal in a desired diagnostic window, as described below. The feedback control module 330 also controls the switching circuit 340 to alternate providing power to the two ultrasound probes 220 in a pulsed fashion, as further described below.

When the feedback control module 330 achieves a steady state acoustic response signal(s), the diagnosis module 345 analyzes an acoustic signature of the acoustic response signal(s) and determines whether a stroke has occurred and, in some examples, whether the stroke is a hemorrhagic stroke or an ischemic stroke. The methodology of this determination by the diagnosis module 345 is described below.

The transducer interface 360 provides for communication between the ultrasound probes 220 and the PCM device 210. For wired transducers, the transducer interface 360 may be a cable connection interface. For wireless transducers, that communicate with the wireless module 370, the transducer interface 360 may be an antenna.

The I/O interface 365 may comprise a control panel that may enable an operator to: 1. turn the device on/off; 2. verify that the ultrasound probes 220 are energized when appropriate; 3. tell how much battery life is left in the power supply 320; 4. select automated adjustment of acoustic output power (via an 'Automated Control' button); 5. select manual adjustment of acoustic power (via a 'Manual Control' button); and 6. provide three LED lights to display the status of the acoustic response during power-up of the ultrasound probes 220. (e.g., Yellow, Green and Red lights).

The feedback control module 330 controls the oscillator circuit 335 to transmit an acoustic wave signal tuned to a nominal frequency ranging between about 100 kHz and about 1000 kHz, e.g., a continuous sine wave signal. The sine wave signal may be amplified to the appropriate power level, as described below, and this signal may be applied to the switching circuit 340 that alternates transmission between two sets of leads to transducers contained in the ultrasound probes 220, for example, every 100 µs, in case the transducers are positioned at the temporal bone on both sides of the patient's head. This transmit power may be applied to the ultrasound transducers that have been positioned and secured to the head of the stroke patient. The transmit power may be coupled to the transducers via the transducer interface 360 to an interconnecting cable, or via the wireless module 370 and an antenna of the transducer interface 360 in the case of wireless transducers. The switching circuit 340 may create, for example, a 100 μs "ON" time followed by a 100 μs "OFF" time for each transducer, such that when one transducer is in the "ON" state, the opposite side transducer is in the "OFF" state. During the transducer "ON" state, the transducer may transmit ultrasound through the patients' skull. During the transducer "OFF" state, the transducer may receive acoustic signals which are communicated back to the feedback control module 330.

The PCM device 210 may communicate with reusable or disposable ultrasound probes 220 which may be wire connected or wirelessly connected to the PCM device 210. The transducers may be placed in an area near the temporal bone area on both sides of the patient's head. The ultrasound probe(s) 220 may be held in place using a gel-like temporary glue, such as used for ECG pads or, alternatively, may be held in place by other means such as, for example, a headband. To provide sufficient conductivity between the ultrasound probe 220 and skin, the hair might be removed at that location, using hair removal cream or clippers. After the ultrasound probes 220 have been positioned, the PCM device 210 may be turned on using the ON/OFF switch. The Yellow control light provides visual confirmation to the user that the system is actually transmitting sound waves. The acoustic output power values after turning the device ON may be in the milliWatts range (e.g., about 20 mW).

Two output power tuning options are available to the user.

Option 1: If the user chooses to press the 'Automated Control' button, the system will automatically increase the acoustic output power until the Green control light turns on. This green light confirms the occurrence of an acoustic response (e.g., oscillation such as, for example, stable cavitation) of the acoustic amplifiers. In one example, stable cavitation may be an acoustic presentation to be used for differentiation between hemorrhagic versus ischemic stroke. The Red control light indicates that the acoustic output power level has exceeded a level normally needed to reach an acoustic response such as, for example, stable cavitation. Excessive output power may cause destruction of the acoustic amplifiers which commonly presents as 'inertial' cavitation. Due to its acoustic properties, inertial cavitation can be distinguished from stable cavitation. Excessive output power may also be identified by an increase in a noise floor of the acoustic signal. In either case, the acoustic output power may be decreased automatically until the desired acoustic response is achieved, at which point, the Red control light turns off and the Green control light turns on.

Option 2: If the user chooses to press the 'Manual Control' button, the system allows the user to increase the acoustic output power manually. The user is advised to increase the output power in such a way that the Green control light is on. If the output power should be exceeded using the 'Manual Control' function the system may either shut down or switch back to the preset function (Yellow control light).

In one example, the diagnostic approach of the PCM device 210 may be based on some mechanism of acoustic response (e.g., stable cavitation, inertial cavitation, sub-harmonics, ultra-harmonics and/or an elevated noise floor), caused by ultrasound excitation of the acoustic amplifiers. The common use of the term 'microbubbles' describes primarily an acoustic amplifier agent designed for diagnostic purposes to enhance image quality. The microbubble concept may be applicable as well to other acoustic amplifier agents not primarily designed for diagnostic purposes. In brief, common diagnostic microbubbles are spheres with an average diameter of 2-3 μm. The shell structure is commonly either a phospholipid or human albumin whereas the inside of the sphere is filled with a perfluorocarbon gas. The agents are administered via a peripheral vein and they are stabilized to pass the lungs to enter the arterial circulation. The half-life of these agents is within the minutes range. Once a microbubble, or other acoustic amplifier, passes an ultrasound field it undergoes frequent pressure changes, leading to either oscillation of the bubble or other acoustic amplifier (e.g., stable cavitation, sub-harmonics, ultra-harmonics) or destruction of the bubble or other acoustic amplifier (e.g., inertial cavitation or an elevated noise floor). Bubble destruction may cause harm to the tissue, specifically the endothelial layer, whereas bubble oscillation has been shown to be affected by a) flow mechanics (e.g., flo/no flow) and b) ambient pressure changes (e.g., elevated intracranial pressure due to hemorrhage). Further, early onset acoustic responses such as bubble oscillation require lower ultrasound energies to occur compared to bubble destruction responses. The Green control light turns on whenever an early onset acoustic response due to acceptable bubble oscillation can be detected, meaning the 'Diagnostic Window' has been reached. Acoustic responses resulting in bubble destruction occur predominantly when energies have been increased beyond the 'Diagnostic Window'. In this case, the Red control light turns on and the Green control light turns off. To accomplish acoustic response control, the transducers may be designed in such a way that they are capable of detecting acoustic response signals whenever they are not transmitting (OFF phase).

Once the device has been set up, the transducer(s) are in place, the intravenous infusion of the acoustic amplifiers should be initiated, and the optimal acoustic output power ultrasound transmission should be started at the earliest time point possible, which means after first aid has been provided and the patient's vital functions have been stabilized. This could be either at a hospital or other location, at the site of the emergency or during patient transport to an admitting hospital. Ultrasound transmission might last until further diagnostic or therapeutic procedures are provided, patient's symptoms are fully resolved, patient's symptoms are worsened, or at any given point in time the care-taking physician recognizes a significant medical indication to discontinue the application.

The ultrasound transducers may be positioned onto the patient's head (or other body region, depending on the application) using a conductive gel, similar to what is being used to keep ECG electrodes fixed to the chest wall, or any other method to hold the transducers in place. The transducers may be positioned on either side of the patient's head, over the temporal bone region forward of the ears. The transducer may be designed for single-use application, and packaged so as to maintain sterility until used. Alternatively, the transducers may be reusable and re-sterilized prior to each use The transducer/gel-pad combination, being pliant, may conform to the shape of the patient's skull (or other body region) and may aid in the transmission of the ultrasound energy into the target region of the brain (or other body region). The gel may have acoustic properties similar to the coupling gel commonly used in ultrasonography. The portion of the gel pad that contacts the patients' skin may have a peel-away strip that exposes a layer of adhesive that helps keep the ultrasound transducer in place and also aids in the transmission of ultrasound energy by helping to eliminate potential air pockets, for instance, in the patients' hair in the application area. Optionally, the shaving of this area might be considered.

Figure 4:
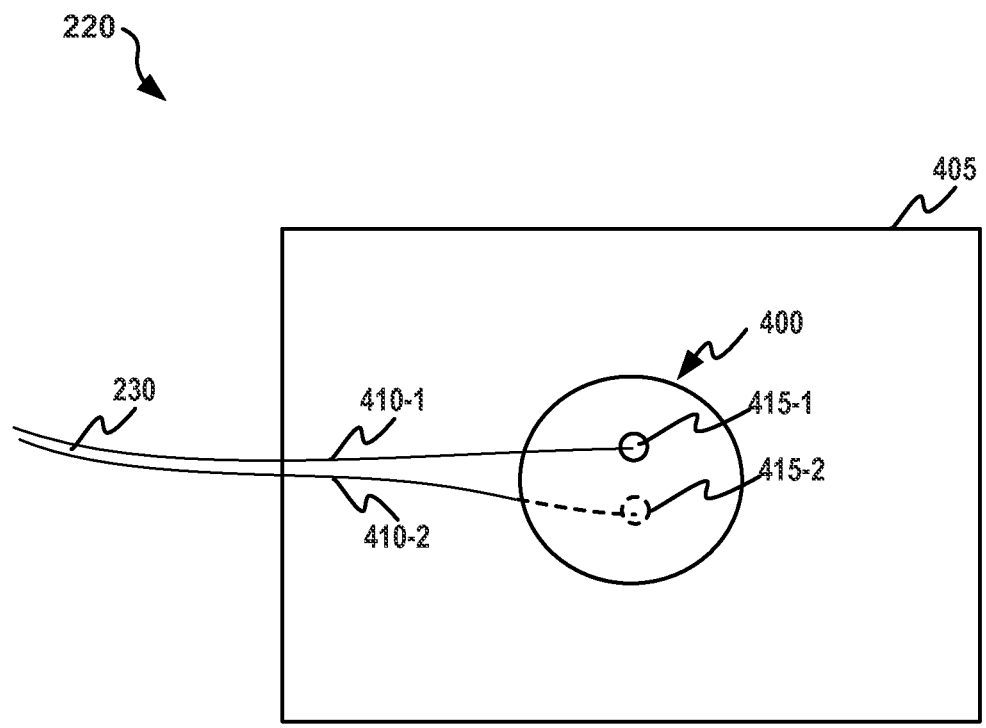
FIG. 4 illustrates an example of an ultrasound probe that may be used in conjunction with the example device of FIG. 3.
Figure 5:
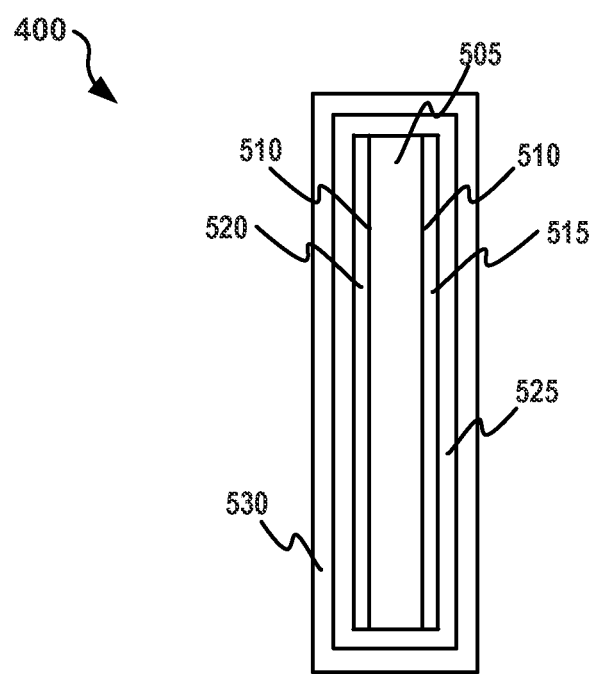
FIG. 5 illustrates an example of an ultrasound transducer that may be included in the example ultrasound probe of FIG. 4.

FIG. 4 illustrates an example of the ultrasound probe 220 that may be used in conjunction with the example PCM device 210 of FIG. 3. FIG. 5 illustrates an example of an ultrasound transducer 400 that may be included in the example ultrasound probe 220 of FIG. 4. The ultrasound probe 220 of FIG. 4 includes the ultrasound transducer 400 with two transducer electrodes 415-1 and 415-2 on opposite sides of the transducer 400. The ultrasound transducer 400 is contained in a gel-pad 405. In the case of a wired transducer 400, the transducer electrodes 415-1 and 415-2 are connected to two electrode leads 410-1 and 410-2, respectively, that come from one of the transducer cables 230 connected to the PCM device 210. Alternatively, the transducer 400 may be equipped with a wireless capability in order to communicate wirelessly with the PCM device 220.

With reference to FIG. 5, the transducer 400, in this example, includes a disk-shaped piezo-electric element 505. The piezo-electric element 505 may be comprised of a piezo-electric material commonly used for medical ultrasound, such as, for example, lead zirconate titanate (PZT). The piezo-electric material, also referred to as the crystal, may have both faces, but not the edge, coated with an electricity-conducting material 510, which may serve as the electrodes 415 of the transducer. The electrode leads 410 may be attached to the electrodes 415 for the purpose of conducting electricity to the crystal and the subsequent generation of ultrasound energy. Other materials may be used for additional coatings as required, such as a quarter-wave matching layer 515 on the side to face the patient to aid in energy transmission, a backing layer 520 on the side away from the patient, a shielding layer 525 to prevent electro-magnetic interference (EMI) and a final insulating coating 530 to prevent inadvertent shock to the patient.

When designed for single use, the transducers 400 may require no housing material or special connectors. The transducers 400 may fit inside the gel-pads 405 in such a way that some thickness of gel will be maintained between the energy-emitting face of the transducer 400 and the patients' scalp. This may be accomplished for instance by incorporating a sleeve in the gel pad 405 into which the transducer may be inserted during the manufacturing process. The electrode leads 410 may exit the gel-pad portions in such a way that they are secured against inadvertent snagging and breakage during emergency deployment.

The transducer 400 may be designed to operate at a frequency of about 100 kHz to 1000 KHz. Experiments have demonstrated that the acoustic field generated using lower transmit frequencies such as these is not subject to distortion as it passes through the skull to the same extent as is the case with higher frequencies in the MHz range. As a result, the acoustic field that is applied to the brain may be designed according to known physical principles with a high degree of predictability. The transducer 400 as described may be flat unfocussed disks with a diameter between 2 cm and 3 cm, such as, for example, a radius between 1 cm and 1.5 cm. In acoustic literature, the transducer radius is typically given the symbol a. The acoustic field emanating from such a transducer may be essentially columnar until it travels a distance d and then it begins to spread in a conical fashion. The distance d is also known as the far-field transition and is given by the equation:

$$d = \frac{a^2}{\lambda} \quad (1)$$

where $\lambda$ is the wavelength of the ultrasound. In water and body tissue at 200 kHz, $\lambda$ is about 0.75 cm. So for a transducer of radius 1 cm, the distance d is about 1.3 cm, and for a radius of 1.5 cm, the distance d is 3 cm. Beyond d, the acoustic energy spreads in a cone shape that is subtended by an angle $\theta$. To be clear, the angle between the acoustic axis and one side of the cone is $\theta$. This angle may be calculated by:

$$\theta = \tan^{-1}\left(\frac{a}{d}\right). \quad (2)$$

It can be seen from these equations that for a given ultrasound frequency, the acoustic beam shape is primarily controlled by the radius of the transducer. Beam shape in turn, will determine the peak intensity of the acoustic field. As the radius of the beam expands according to the angle $\theta$, the beam intensity decreases as the square of the radius. The beam intensity may also decrease with distance due to attenuation by the brain tissue. These effects may come into play during the discussion of safety and the possibility of creating standing waves in the cranium.

The following example illustrates an example design, operation and inherent safety of the proposed therapeutic device. A transducer of radius 1.5 cm will have transition distance of 3 cm. This is near the point of peak acoustic intensity because beyond this, the beam becomes wider. If the transducer power has been adjusted to produce for instance 600 mW/cm2 acoustic intensity at this point, then at 5 cm depth the intensity typically drops off to less than 300 mW/cm$^2$, and at 6 cm to about 125 mW/cm$^2$. Given an average skull diameter of 16 cm, the acoustic intensity of the beam may be on the order of 20 mW/cm$^2$ by the time it reaches the opposite skull surface. Any standing waves generated by reflection at the contralateral interior skull surface should be of negligible amplitude. And yet, the ultrasound intensity that is most likely to have a therapeutic effect is contained in the clinically relevant depth of 30-60 mm depth on the ipsilateral side of the brain midline.

A pulse duration between 10-1000 μs may be employed with about a 1-50% duty cycle. At a frequency of about 200 kHz. This is a convenient paradigm in another sense because the wavelength for this frequency is about 7.5 mm in soft tissue. A 20-cycle burst, given, for example, a pulse duration of 100 μs and a duty cycle of 50%, would be 15 cm in total length, or nearly the diameter of the average cranium from one temporal bone to the other. If the two transducers alternated their active times, which may be defined as the ON-time, the acoustic field of one transducer would be much diminished where the energy of the other transducer passed through at the same time, and this strategem may also minimize the likelihood of creating standing waves. In the power unit, to be described below, a simple circuit can be devised in which a 200 kHz CW signal, for example, is switched from one set of conductors to another set every 100 μs to create the alternating 20 cycle bursts from the opposing transducers.

In one example, design, considerations include that during the OFF-time, the transducer has the capability to receive acoustic signals. Since it is suggested that different acoustic response signals (e.g., stable or inertial cavitation, sub-harmonics, ultra-harmonics, and/or noise floor level) may be used to assess biophysical effects including a) whether or not there is a stroke, and b) to differentiate between ischemic or hemorrhagic stroke. The interpretation of the acoustic response signals may be based on known acoustic response signatures such as, for example, the presence or lack of sub-harmonic and/or ultra-harmonic frequencies. For example, at a give transmit frequency of 200 KHz, a range of frequencies near the sub-harmonic frequency of 100 kHz as well as a range of frequencies near the ultra-harmonic frequency of 300 kHz may be assessed. The occurrence of acoustic responses in both these frequency ranges may indicate the presence of oscillation of the acoustic amplifiers and therefore describes the individual 'Diagnostic Window'. In contrast, the occurrence of an increased area under the acoustic response curve in an area of the fundamental frequency of 200 kHz, in this example, and/or a raise of the noise floor indicate high energy levels outside of the 'Diagnostic Window' and may be indicative of abnormal events (e.g., inertial cavitation or acoustic amplifier destruction). Sub-harmonic and ultra-harmonic frequencies may still be present in such a scenario, but may not be dominant. In the case of these high energy levels outside of the 'Diagnostic Window', the system may automatically lower the acoustic output until only those acoustic response signals representing sub-harmonic, ultra-harmonic and/or higher harmonics can be detected (when using 'Automated Control' option) or, alternatively, the system may be shut down instantaneously or automatically reset to its preset (when using the 'Manual Control' option).

The transducer design considerations may provide a guaranteed minimum half-life of 24 hours. For subacute/chronic applications, the requirements for the transducer half-life may be different in the sense of longer term durability, assuming proper care and maintenance in a controlled environment (e.g., hospital, rehabilitation center, retirement home).

One example method of using the acoustic response signature for differential diagnosis takes advantage of the probability that an acute stroke is commonly a unilateral event. This implies that the cause of a stroke, whether it is an acute blockage (in case of ischemia) or a rupture (in case of hemorrhage) of a brain artery, occurs locally in a certain vessel territory in one of the two brain hemispheres. In other words, the acute disease is unilateral. Taking this into consideration one can assume that the contralateral hemisphere is not affected by the same event. In this case, the unaffected contralateral hemisphere might be used as an intra-individual or internal baseline reference. It may be assumed that the acoustic response presentation in the unaffected hemisphere is within normal ranges whereas the acoustic response in the affected hemisphere may be abnormal. Alternatively to comparing the two acoustic responses to each other, both acoustic responses may be compared to a predetermined baseline acoustic response, or range of acoustic responses, known to be normal and an abnormal condition may be made for both in reference to the known normal response(s).

Normal Acoustic Response Signature—A normal acoustic response may be defined as an acoustic response signature presented as described above, showing normal expected levels of sub-harmonics as well as ultra-harmonics or higher harmonics without an elevation of a noise floor.

Abnormal Acoustic Response Signature—An abnormal acoustic response may be defined as an acoustic response signature which deviates in signal amplitude from the normal expected acoustic response(s), such as, due to the presence/absence of different levels of sub-harmonics, ultra-harmonics, higher harmonics, an elevation of the noise floor, etc. as described below.

An example diagnosis for differentiating between a hemorrhagic stroke and an ischemic stroke will now be described. This is only an example and other methods may be used.

It has been shown that a change in ambient pressure has an impact on the strength of the acoustic response signature of acoustic amplifiers. Increasing ambient pressure around a vessel leads to a decrease in signal amplitude of the acoustic response at certain frequencies.

This means that fundamental, sub-, ultra-, and higher harmonics might be present but diminished in comparison to the acoustic response signature presentation of the other, unaffected brain hemisphere or a known normal signature being used as a baseline. In case of a hemorrhage, blood enters the extravascular space and/or the brain parenchyma. Since the interior of the human skull is a closed environment, the ambient pressure increases, resulting in a decreased amplitude of the acoustic response signal. Since the vessels are not blocked, replenishment of microbubbles is provided enabling continuous signal acquisition at a comparable level. This means that a diminished stable cavitation signature could be monitored over a longer period of time to the same extent or, in case of increasing ambient pressure over time, a further signal decrease could be expected.

Leading Criterion Indicative of Hemorrhagic Stroke—Diminished signal amplitude in comparison to the unaffected hemisphere or a known normal signature used as a baseline acoustic response signature.

In case of ischemic stroke, a feeding artery is blocked by a blood clot. If such an event occurs in a larger sized vessel (e.g., proximal part of the middle cerebral artery), the entire supply area distal to the occlusion will not be perfused with microbubbles or other acoustic amplifiers. If microbubbles or other acoustic amplifiers are not present, acoustic response signals cannot be detected on the affected side and the detected acoustic signature is absent in comparison to the unaffected hemisphere or a known normal signature used as a baseline. In case of sufficient collateralization of the affected territory, acquisition of acoustic response signals may be possible to a similar extent (e.g., signal amplitude) compared to the unaffected hemisphere or a baseline signature. However, since collateral vascular pathways are represented by very small sized arterioles or capillaries, the replenishment with microbubbles or other acoustic amplifiers in this area can be expected to be delayed because of the reduced flow velocity in small sized vessels. Given the scenario described above, it can be further expected that the acoustic response presentation will exhaust quickly over time (e.g., declining signal amplitude within a couple of frames).

Lending Criterion Indicative For Ischemic Stroke—No signal/fast signal exhaustion in comparison to the unaffected hemisphere or a known normal signature used as a baseline acoustic response signature.

In case of absence of either an ischemic or an hemorrhagic event, it may be assumed that the diagnostic region of interest is neither affected by absence of, or reduced, microbubble or other acoustic amplifier replenishment (e.g., vessel occlusion in ischemic stroke), nor diminished signal amplitude presentation (e.g., increased ambient pressure in hemorrhagic stroke). In these cases, the acoustic response signature should be comparable in both brain hemispheres due to the lack of pathology.

Leading Criterion Indicative For Absence of Ischemic/Hemorrhagic Stroke—Comparable acoustic response signature in both hemispheres.

Figure 6:
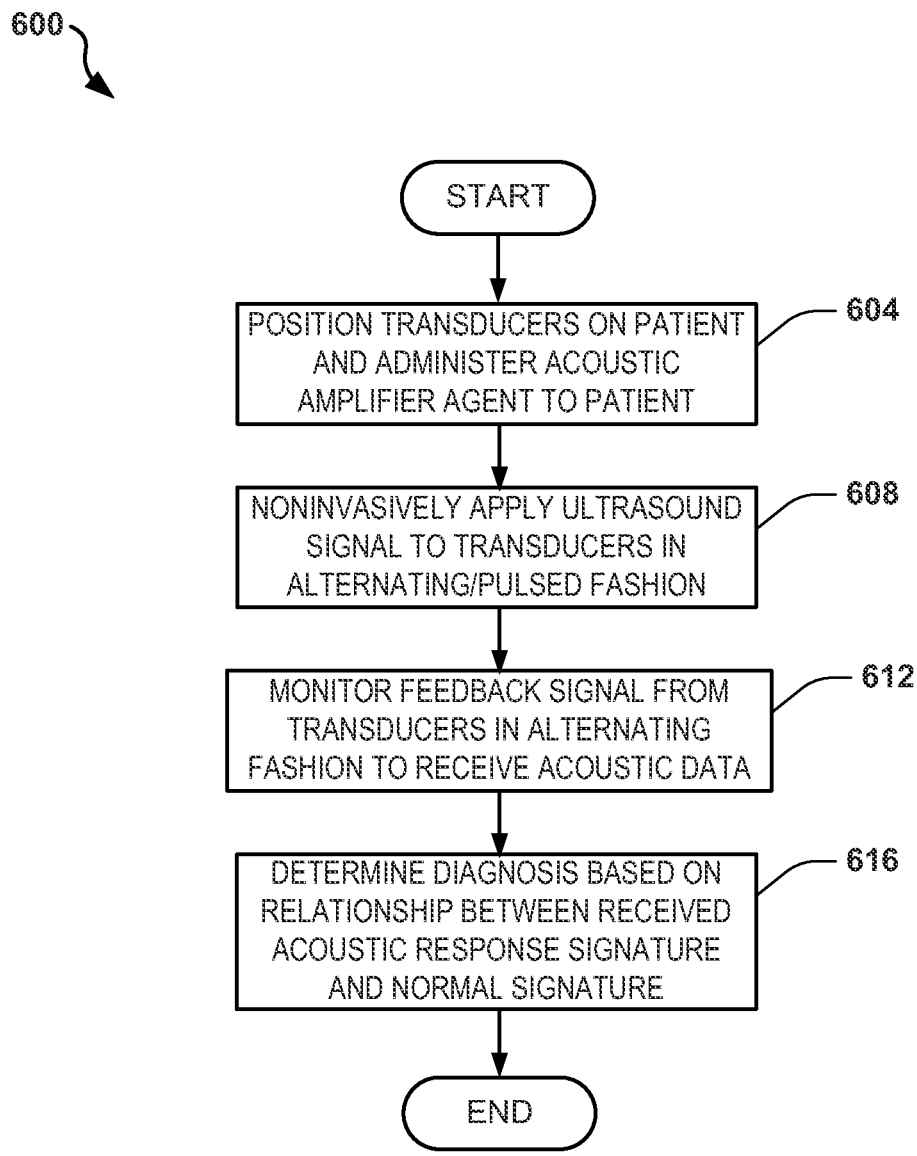
FIG. 6 is a flow chart of an example process for providing treatment of a stroke victim.

FIG. 6 is a flow chart of an example process 600 for providing treatment of a stroke victim. The process 600 is exemplary only and stages may be combined, rearranged and/or omitted. The process 600 may be performed by the PCM device 210 described above. The process 600 may be performed in the field for cases where the PCM device 210 is a portable device, or may be performed in a facility for cases where the PCM device 210 is a fixed device (e.g., in an emergency room) or is integrated within another piece of diagnostic or medical equipment. The process 600 will be described with further reference to components of the PCM device 210 shown in FIG. 3.

The process 600 may begin at stage 604 with a user positioning transducers on a patient and administering an acoustic amplifier agent intravenously to the patient. The transducers may be contained in an ultrasound probe such as, the ultrasound probe 220 shown in FIG. 4 and the user may peel off the peel-away strip to expose the adhesive and place the transducers on the patient (e.g., in the area of the temporal bone close to each ear). The acoustic amplifier agent may include microbubbles, liposomes, acoustic spheres, or some other acoustic amplifier.

At stage 608, the feedback control module 330 causes the oscillator circuit 355 to noninvasively apply an ultrasound signal to the transducers in an alternating and pulsed fashion, as described above. The ultrasound signal may be applied at a preset power level to begin, and the feedback control module 330 may adjust the power up or down, as described above, based on the nature of acoustic response signals received from the transducers. As described above, the ultrasound signal may be applied to a first of the transducers in a first On-time and applied to a second of the transducers in a second On-time that may coincide with an Off-time of the first transducer.

At stage 612, the feedback control module 330 monitors feedback acoustic response signals from the transducers in an alternating fashion to receive acoustic data that is used to generate acoustic response signatures of the acoustic response signals. The feedback acoustic response signals may be received via cables, or via the wireless communications module 370. The feedback acoustic response signal of the first transducer may be received during the first Off-time of the first transducer (where the first Off-time of the first transducer may correspond to the second On-time of the second transducer), and the feedback acoustic response signal of the second transducer may be received during the second Off-time of the second transducer (where the second Off-time of the second transducer may correspond to the first On-time of the first transducer).

The application of the ultrasound signal at stage 608 and the monitoring of the feedback acoustic response signal at stage 612, may continue until an acoustic response (e.g., stable cavitation) is achieved, until the noise floor of the acoustic response signature is elevated (indicating inertial cavitation), or until a time limit is exceeded. If the time limit is exceeded, the process 600 may be stopped and/or started over. During this time period, the power level of the applied ultrasound signal may be increased and/or decreased in order to determine the acoustic response signature of each of the transducers.

Upon successfully determining the acoustic response signature of each of the transducers, the diagnosis module 345 may determine a diagnosis of stroke at stage 616 based on a comparison of the acoustic response signatures of the feedback acoustic response signals in relation to a baseline (e.g., normal) acoustic response signature. The baseline acoustic response signature may be stored in the memory 315 of the PCM device 210. Alternatively, the baseline acoustic response signature could be one of the acoustic response signature determined by monitoring one of the feedback acoustic response signatures at block 612. This alternative method may be sufficient for most stroke cases where the stroke is present in only one side of the patient's skull. This diagnosis at stage 616 may be made in accordance with the criteria described above. The diagnosis may include whether or not a stroke is present in the patient and/or whether the stroke is a hemorrhagic stroke or an ischemic stroke.

Figure 7:
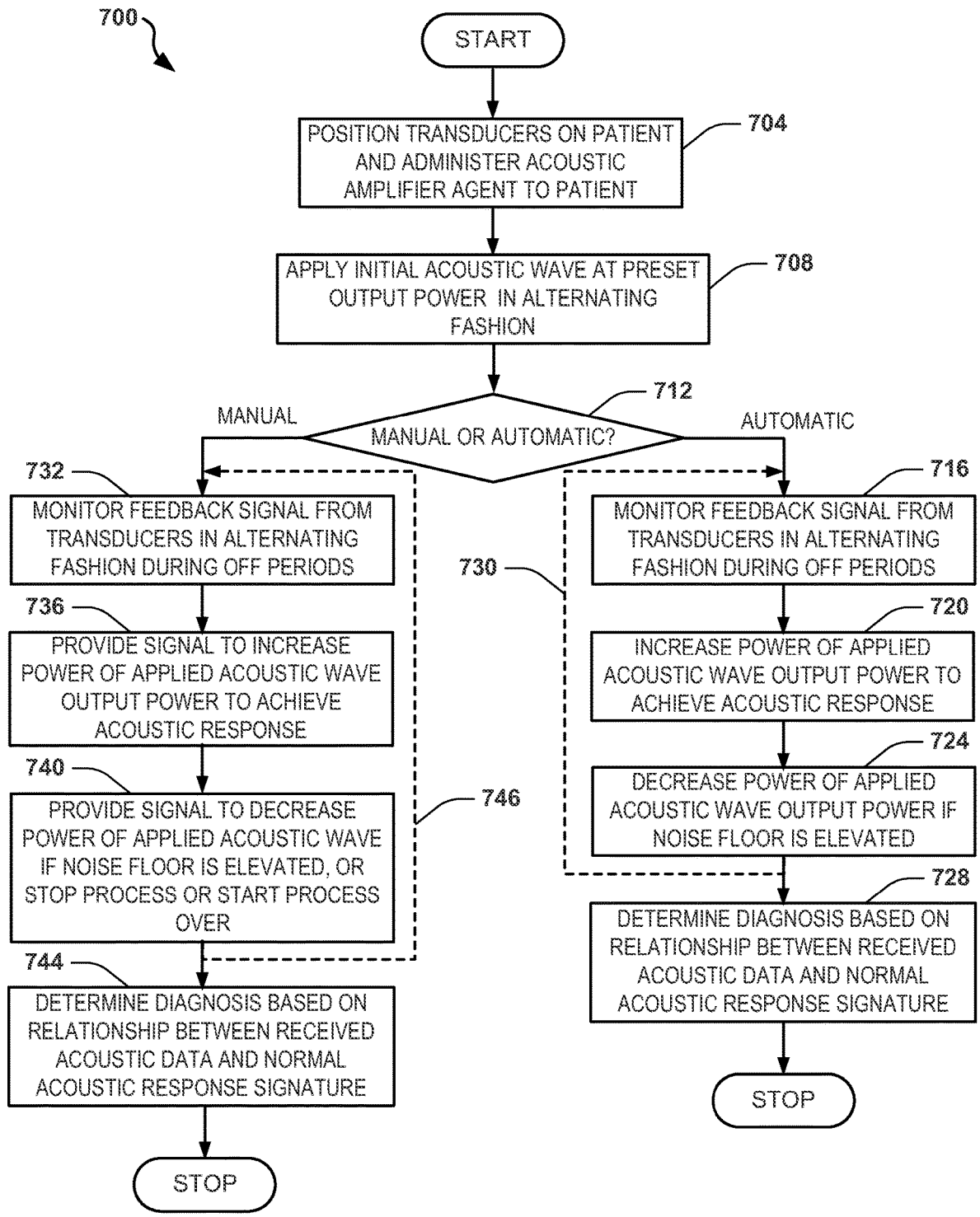
FIG. 7 is a flow chart of another example process for providing treatment of a stroke victim.

FIG. 7 is a flow chart of another example process 700 for providing treatment of a stroke victim. The process 700 is exemplary only and stages may be combined, rearranged and/or omitted. The process 700 may be performed by the PCM device 210 described above. The process 700 may be performed in the field for cases where the PCM device 210 is a portable device, or may be performed in a facility for cases where the PCM device 210 is a fixed device (e.g., in an emergency room) or is integrated within another piece of diagnostic or medical equipment. The process 700 will be described with further reference to components of the PCM device 210 shown in FIG. 3.

The process 700 may begin at stage 704 with a user positioning transducers on a patient and administering an acoustic amplifier agent intravenously to the patient. The transducers may be contained in an ultrasound probe such as, the ultrasound probe 220 shown in FIG. 4 and the user may peel off the peel-away strip to expose the adhesive and place the transducers on the patient (e.g., in the area of the temporal bone close to each ear). The acoustic amplifier agent may include microbubbles, liposomes, acoustic spheres, or some other acoustic amplifier.

At stage 708, the feedback control module 330 causes the oscillator circuit to noninvasively apply an ultrasound signal at a preset power level to the transducers in an alternating and pulsed fashion, as described above. The preset power level may be based on certain criteria of the patient. For example, the preset power level may be based on a race, age and gender of the patient. FIG. 8 is a Table showing an array of preset power settings ($PS_{m \cdot n}$) that may be determined by testing groups of individual fitting the race, age and gender criteria. For example, the Table of FIG. 8 lists $PS_{m \cdot n}$ variables for three age groups: less than 45 years, 45-65 years and greater than 65 years. Other age groups may be used. The Table of FIG. 8 also shows four ethnicities: Caucasian (m=1, 2, 3), Hispanic (m=4, 5, 6), Asian (m=7, 8, 9) and African-American (m=10, 11, 12). Other ethnicities may be used. Thus, there are 24 $PS_{m \cdot n}$ variables that are determined for the four races, three ages and two genders.

The user may be queried at stage 708 by the I/O interface 365 to input the race, age and gender of the patient. In response to the user input, the feedback control module 330 sets the preset output power to the proper level, as determined by the $PS_{m \cdot n}$ variable corresponding to the received user input.

At decision block 712, the I/O interface 365 queries the user to select whether to perform the tuning of the power level manually (e.g., by the user pushing a "Manual Control" button on a control panel) or automatically (e.g., by the user pushing an "Automatic Control" button on the control panel). If the user selects the automatic control mode, the process 700 proceeds to stage 716. If the user selects the manual control mode, the process 700 proceeds to stage 732.

For the automatic control mode, at stage 716, the feedback control module 330 monitors feedback acoustic response signals from the transducers in an alternating fashion to receive acoustic data that is used to generate an acoustic response signatures of the acoustic response signals. The feedback acoustic response signals may be received via cables, or via the wireless communications module 370. The feedback acoustic response signal of the first transducer may be received during the first Off-time of the first transducer (where the first Off-time of the first transducer may correspond to the second On-time of the second transducer), and the feedback acoustic response signal of the second transducer may be received during the second Off-time of the second transducer (where the second Off-time of the second transducer may correspond to the first On-time of the first transducer).

At stage 720, the feedback control module 330 increases the power to achieve acoustic response signals received from the transducers. At stage 724, the feedback control module 330 decreases the power if the noise floor of the acoustic response signal exhibits an elevated level. As described above, the ultrasound signal may be applied to a first of the transducers in a first On-time and applied to a second of the transducers in a second On-time that may coincide with an Off-time of the first transducer.

The monitoring at stage 716, the increasing power at stage 720, and the decreasing power at stage 724 may continue (as indicated by the dashed arrow 730) until an acoustic response signature is able to be derived from the feedback acoustic response signals, until the noise floor remains elevated, or until a time limit is exceeded. If the time limit is exceeded, the process 700 may be stopped and/or started over.

Figure 9:
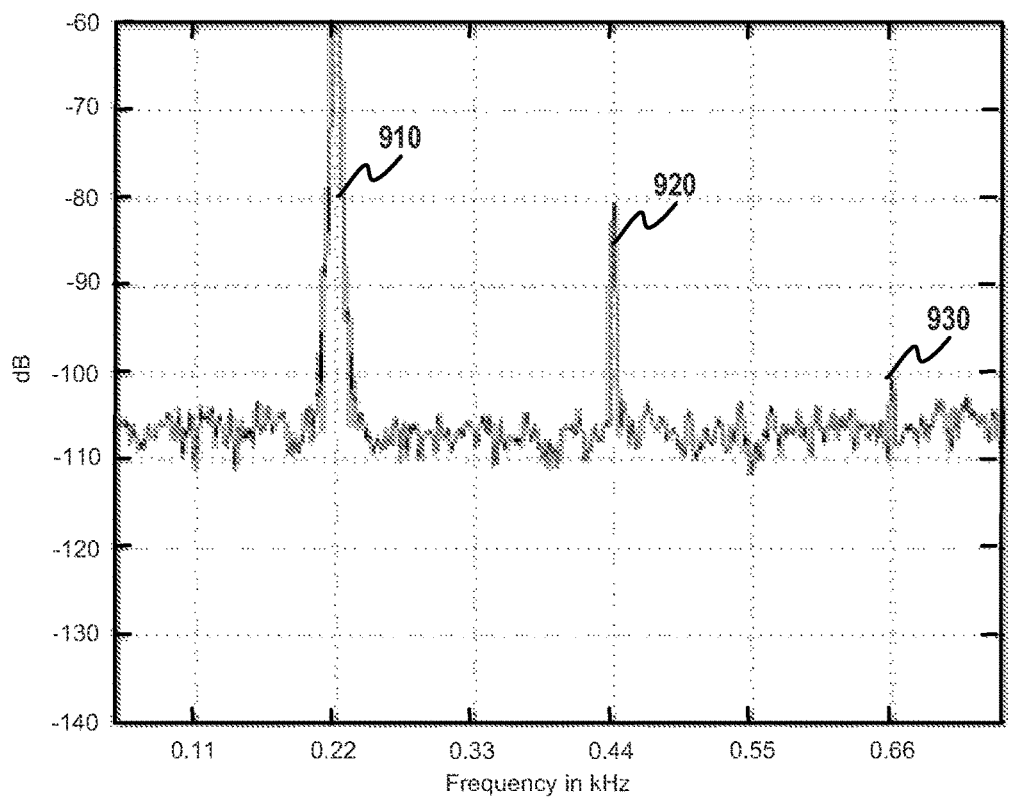
FIG. 9 is a graph illustrating an example of typical spectrum with an absence of acoustic response signals caused by ultrasound excitation of acoustic amplifiers.
Figure 10:
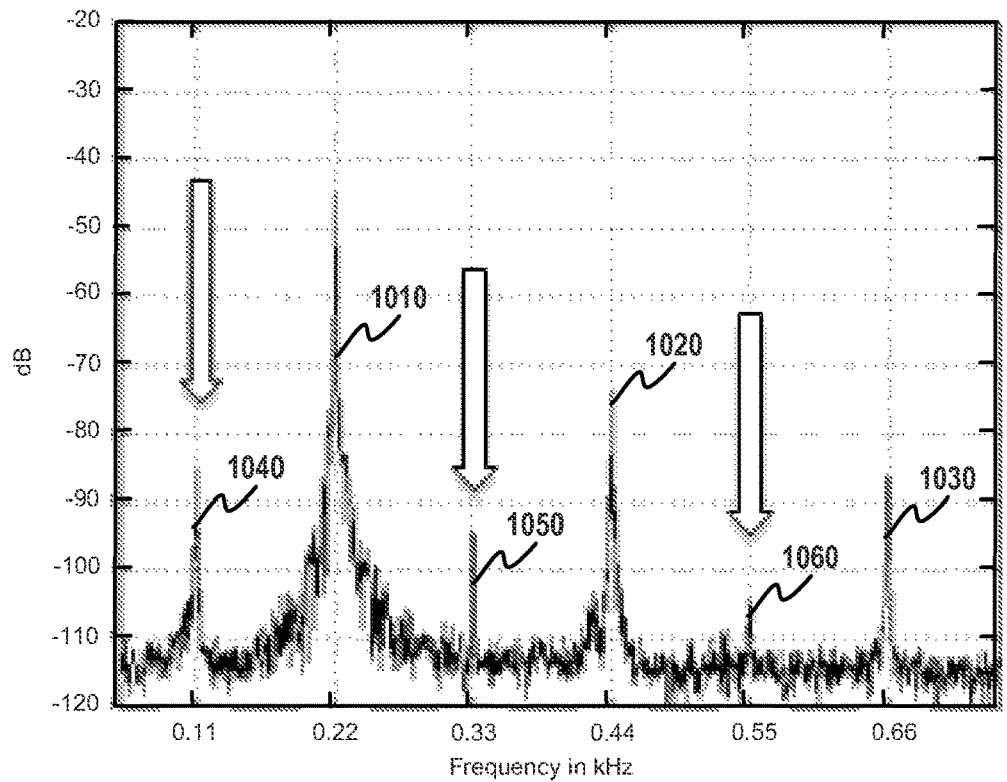
FIG. 10 is a graph illustrating an example of typical spectrum with presence of acoustic response signals caused by ultrasound excitation of acoustic amplifiers.

FIGS. 9 and 10 illustrate examples of graphs illustrating respective examples of typical spectrum with an absence of acoustic response signals caused by ultrasound excitation of acoustic amplifiers (FIG. 9) and with a presence of acoustic response signals caused by ultrasound excitation of acoustic amplifiers (FIG. 10).

With reference to FIG. 9, an example acoustic response exhibits a main peak 910 at a center frequency. In this example, the center frequency corresponds to a transmit frequency of 220 kHz. In addition, a second harmonic peak 920 appears at 440 kHz and a third harmonic peak 930 appears at 660 kHz. The first, second and third harmonic peaks 910, 920 and 930 appear when the initial acoustic wave is applied at stage 708 at the preset output power, even if the acoustic amplifiers are not present. In this example, an acoustic response signal of the acoustic amplifiers is not achieved at the preset power output level and, as a result, the power of the applied acoustic wave is increased at stage 720 until an acoustic response signal of the acoustic amplifiers is achieved.

With reference to FIG. 10, an example acoustic response, where an acoustic response signal of the acoustic amplifiers is achieved, exhibits first, second and third harmonic peaks 1010, 1020 and 1030, respectively, at the transmit frequency of 220 kHz, at 440 kHz and at 660 kHz, as appeared in the graph of FIG. 9. In addition, acoustic response signals caused by ultrasound excitation of acoustic amplifiers (microbubbles in this example) appear as peaks 1040, 1050 and 1060, respectively, at 110 kHz, 330 kHz and 550 kHz. As soon as such a signature, as illustrated in FIG. 10, can be detected, the increases in output power at stage 720 would be stopped and the resulting acoustic response signature would be stored in memory for diagnosis at stage 728.

Upon successfully determining the acoustic response signature of each of the transducers, the diagnosis module 345 may determine a diagnosis of stroke at stage 728 based on a comparison of the acoustic response signatures of the feedback acoustic response signals in relation to a baseline (e.g., normal) acoustic response signature. The baseline acoustic response signature may be stored in the memory 315 of the PCM device 210. Alternatively, the baseline acoustic response signature could be one of the acoustic response signature determined by monitoring one of the feedback acoustic response signatures at block 716. This alternative method may be sufficient for most stroke cases where the stroke is present in only one side of the patient's skull. This diagnosis at stage 728 may be made in accordance with the criteria described above. The diagnosis may include whether or not a stroke is present in the patient and/or whether the stroke is a hemorrhagic stroke or an ischemic stroke. For example, using the acoustic response signature illustrated in FIG. 10, the diagnosis may identify a) a loss of non-linear response at acoustic amplifier excitation frequencies of 110 kHz (peak 1040), 330 kHz (peak 1050) and 550 kHz (peak 1060) (e.g. a possible ischemic event), b) a presence of non-linear response at acoustic amplifier excitation frequencies of 110 kHz (peak 1040), 330 kHz (peak 1050) and 550 kHz (peak 1060), but at reduced signal amplitudes (e.g. a possible hemorrhagic event) or c) a similar non-linear response (e.g. neither ischemic nor hemorrhagic event).

If the user selects the manual control mode, the process 700 proceeds to stages 732, 736, 740 and 744. The functions performed at stage 732 are similar to those performed at stage 716. The functions performed at stages 736 and 740 are similar to those performed at stages 720 and 724, except that instead of the feedback control module 330 automatically increasing and/or decreasing the output power automatically, the user is signaled by the feedback control module 330 to manually adjust the output power. In one example, as described above, the user is signaled via the Red, Green and Yellow lights to increase and/or decrease the output power.

The monitoring at stage 732, the increasing power at stage 736, and the decreasing power at stage 740 may continue (as indicated by the dashed arrow 746) until an acoustic response signature is able to be derived from the feedback acoustic response signals, until the noise floor remains elevated, or until a time limit is exceeded. If the time limit is exceeded, the process 700 may be stopped and/or started over.

Upon successfully determining the acoustic response signature of each of the transducers, the diagnosis module 345 may determine a diagnosis of stroke at stage 744 based on a comparison of the acoustic response signatures of the feedback acoustic response signals in relation to a baseline (e.g., normal) acoustic response signature. The baseline acoustic response signature may be stored in the memory 315 of the PCM device 210. Alternatively, the baseline acoustic response signature could be one of the acoustic response signature determined by monitoring one of the feedback acoustic response signatures at block 732. This alternative method may be sufficient for most stroke cases where the stroke is present in only one side of the patient's skull. This diagnosis at stage 744 may be made in accordance with the criteria described above. The diagnosis may include whether or not a stroke is present in the patient and/or whether the stroke is a hemorrhagic stroke or an ischemic stroke.

Concepts described in this proposal, including using an exemplary device, or a device or combination of devices employing all or part of an exemplary method to diagnose stroke victims, may be generally applicable to other ischemic diseases caused by embolic or thrombo-embolic events, such as myocardial infarction (MI) or deep vein thrombosis (DVT). Underlying cause for all these diseases is the sudden occlusion of a vessel by a blood clot with the consequence of consecutive cell death in the supplied area due to lack of oxygen supply. All these diseases have in common the acuity of onset and the need for a therapeutic option at the earliest time point possible. Hence, a diagnosis using techniques similar to those described above may be reasonable. An optional design consideration could be to expand transducer designs as well as ultrasound sequences, dedicated for other ischemic diseases, such as MI or DVT.

The communication between paramedic teams 'in the field' and medical personal in the receiving hospital is very sparse. An optional design consideration could be to build-in wireless capability into the device to transmit real-time data from the device directly to an allocated server at the receiving hospital using 3G/4G bandwidth technologies.

Referring to the basic, underlying pathologies of ischemic events the innovation may be applicable to ischemic diseases in any organ system, except the lung. This would include, e.g., mainly: 1. Stroke, 2. Myocardial Infarction, 3. Deep Vein Thrombosis, and 4. Arterio-Venous Shunt occlusions. According to the underlying pathology and location the transducer design as well as the diagnostic sequences would have to be adapted.

The significance of a device as described herein is that it would provide a method and a device to diagnose stroke and its potential cause already in the field, during the transport of the patient to the hospital, or at any given patient location. It would provide the capability to adjust automatically to the individual diagnostic window for each single patient which is crucial because of the significant differences in skull morphology between humans of different age, gender and race. Further, it describes the combinational use of acoustic amplifiers, such as microbubbles for example, and acoustic response signals, caused by the latter, as the underlying mechanism for the differential diagnosis of stroke. Worldwide, there is currently no other pre-hospital diagnostic strategy or device which could achieve is capable of providing such diagnostic capabilities. Millions of patients, who suffer from acute stroke-like syndromes, could be diagnosed already in the pre-hospital environment and referred to the appropriate hospital where, for example, tPA treatment (in case of ischemic stroke) or neuro-intervention (in case of hemorrhage) could be provided. The use of this approach could become future Standard of Care for the diagnosis of acute stroke in the field, or anywhere else, much like the defibrillator became Standard of Care for cardio-conversion.

Various examples described herein are described in the general context of method steps or processes, which may be implemented in one example by a software program product or component, embodied in a machine-readable medium, including executable instructions, such as program code, executed by entities in networked environments. Generally, program modules may include routines, programs, objects, components, data structures, etc. that perform particular tasks or implement particular abstract data types. Executable instructions, associated data structures, and program modules represent examples of program code for executing steps of the methods disclosed herein. The particular sequence of such executable instructions or associated data structures represents examples of corresponding acts for implementing the functions described in such steps or processes.

The foregoing description of various examples has been presented for purposes of illustration and description. The foregoing description is not intended to be exhaustive or limiting to the precise form disclosed, and modifications and variations are possible in light of the above teachings or may be acquired from practice of various examples. The examples discussed herein were chosen and described in order to explain the principles and the nature of various examples and its practical application to enable one skilled in the art to utilize the various examples and with various modifications as are suited to the particular use contemplated. The features of the examples described herein may be combined in all possible combinations of methods, apparatus, modules, systems, and computer program products.

What is claimed is:

1. A method comprising:
    applying, to at least one transducer, an ultrasound signal to cause the at least one transducer to transmit ultrasound to a location on a patient's body;
    administering acoustic amplifiers intravenously to the patient, the acoustic amplifiers including microbubbles, the microbubbles including a shell filled with a gas such that the microbubbles are stabilized to pass through lungs of the patient;
    monitoring a feedback acoustic response signal from the at least one transducer to receive data indicative of an acoustic response of the acoustic amplifiers triggered by the ultrasound;
    controlling a power of the ultrasound such that acoustic response signals representing at least subharmonics or ultra-harmonics, or both, are measured in the monitored feedback acoustic signal;
    and
    differentiating between an occurrence of a hemorrhagic stroke and an ischemic stroke, and an absence of the hemorrhagic stroke or the ischemic stroke based at least in part on a relationship between an acoustic response signature of the feedback acoustic response signal and a baseline acoustic response signature,
    wherein the differentiating further comprises
    determining that the hemorrhagic stroke has occurred if the acoustic response signature including the measured sub-harmonics or ultra-harmonics or both, exhibits a diminished signal amplitude in comparison to the baseline acoustic response signature,
    determining that the ischemic stroke has occurred if the acoustic response signature including the measured sub-harmonics or ultra-harmonics or both, exhibits signal exhaustion or no signal in comparison to the baseline acoustic response signature, and
    determining that the absence of the hemorrhagic stroke or the ischemic stroke has occurred if the acoustic response signature exhibits a common acoustic response signal in both brain hemispheres,
    wherein the baseline acoustic response signature corresponds to an unaffected brain hemisphere or a known normal acoustic response signature.

2. The method of claim 1, wherein the at least one transducer includes a plurality of transducers and the ultrasound signal is applied in an alternating pattern and pulsed fashion.

3. The method of claim 2, wherein the at least one transducer comprises a first transducer and a second transducer and applying the ultrasound signal comprises:
    applying a first pulse of ultrasound during a first On-time period with the first transducer; and
    applying a second pulse of ultrasound during a second On-time period with the second transducer, the second On-time period being outside of the first On-time period.

4. The method of claim 3, wherein the monitoring comprises:
receiving a first feedback acoustic response signal from the first transducer during the second On-time period; and
receiving a second feedback acoustic response signal from the second transducer during the first On-time period.

5. The method of claim 1, wherein the ultrasound signal is applied to a patient's skull, and the method further comprising diagnosing at least one of presence of the hemorrhagic stroke and presence of the ischemic stroke based at least in part on the relationship between the acoustic response signature and the baseline acoustic response signature.

6. The method of claim 5, wherein, the at least one transducer comprises two transducers and the baseline acoustic response signature comprises at least one of a known normal acoustic response signature, and an acoustic response signature corresponding to an unaffected hemisphere, wherein the baseline acoustic response signature is obtained from one of the two transducers.

7. The method of claim 1, wherein applying the ultrasound signal comprises applying the ultrasound signal in accordance with at least one of patient age, patient race, and patient gender.

8. A system, comprising:
two ultrasound transducer elements configured to provide ultrasound to a patient;
a power and control module (PCM) device communicatively coupled to the two ultrasound transducer elements and configured to:
control an application of the ultrasound to trigger an acoustic response from acoustic amplifiers infused into the patient, the acoustic amplifiers including microbubbles, the microbubbles including a shell filled with a gas such that the microbubbles are stabilized to pass through lungs of the patient; and
monitor a feedback acoustic response signal from the two ultrasound transducer elements to receive data indicative of the acoustic response, and wherein a power of the applied ultrasound is controlled such that acoustic response signals representing at least sub-harmonics or ultra-harmonics, or both, are measured in the monitored feedback acoustic response signal; and
use an acoustic response signature of the feedback acoustic response signal to enable a diagnosis based at least in part on a relationship between the acoustic response signature and a baseline acoustic response signature, the diagnosis including differentiating between an occurrence of a hemorrhagic stroke, an ischemic stroke and an absence of the hemorrhagic stroke or ischemic stroke,
wherein the differentiating further comprises
determining that the hemorrhagic stroke has occurred if the acoustic response signature including the measured sub-harmonics or ultra-harmonics, or both, exhibits a diminished signal amplitude in comparison to the baseline acoustic response signature,
determining that the ischemic stroke has occurred if the acoustic response signature including the measured sub-harmonics or ultraharmonics, or both, exhibits signal exhaustion or no signal in comparison to the baseline acoustic response signature, and
determining that the absence of the hemorrhagic stroke or the ischemic stroke has occurred if the acoustic response signature exhibits a common acoustic response signal in both brain hemispheres,
wherein the baseline acoustic response signature correspond to an unaffected brain hemisphere or a known normal acoustic response signature.

9. The apparatus of claim 8, wherein the PCM device is communicatively coupled wirelessly to the two ultrasound transducer elements.

10. The apparatus of claim 8, wherein the PCM device is further configured to allow selection of a manual control mode or an automatic control mode for controlling the application of the ultrasound.

11. The apparatus of claim 8, wherein the two ultrasound transducer elements are configured to provide the ultrasound to a patient's skull, and the PCM device is further configured to diagnose at least one of presence of the hemorrhagic stroke and presence of the ischemic stroke based at least in part on the relationship between the acoustic response signature and the baseline acoustic response signature.

12. The apparatus of claim 11, wherein, the baseline acoustic response signature comprises at least one of a known normal acoustic response signature, and an acoustic response signature corresponding to an unaffected hemisphere, wherein the baseline acoustic response signature is obtained from one of the two ultrasound transducer elements.

13. An apparatus comprising:
a processor;
a non-transitory memory storing program code, the program code for causing the processor to:
apply, to at least one transducer, an ultrasound signal to cause the at least one transducer to transmit ultrasound to a location on a patient's body, the ultrasound signal to trigger an acoustic response of acoustic amplifiers infused into the patient, the acoustic amplifiers including microbubbles, the microbubbles including a shell filled with a gas such that the microbubbles are stabilized to pass through lungs of the patient;
monitor a feedback acoustic response signal from the at least one transducer to receive data indicative of the acoustic response of the acoustic amplifiers, and wherein a power of the applied ultrasound is controlled such that acoustic response signals representing at least sub-harmonics or ultra-harmonics, or both, are measured in the monitored feedback acoustic response signal; and
differentiate between an occurrence of a hemorrhagic stroke, an ischemic stroke and an absence of the hemorrhagic stroke or ischemic stroke based at least in part on a relationship between an acoustic response signature of the feedback acoustic response signal and a baseline acoustic response signature,
wherein the differentiate includes
determining that the hemorrhagic stroke has occurred if the acoustic response signature including the measured sub-harmonics or ultra-harmonics, or both, exhibits a diminished signal amplitude in comparison to the baseline acoustic response signature, determining that the ischemic stroke has occurred if the acoustic response signature including the measured sub-harmonics or ultra-harmonics, or both, exhibits signal exhaustion or no signal in comparison to the baseline acoustic response signature, and
determining that the absence of the hemorrhagic stroke or the ischemic stroke has occurred if the acoustic response signature exhibits a common acoustic response signal in both brain hemispheres, wherein the baseline acoustic response signature corresponds to an unaffected brain hemisphere or a known normal acoustic response signature.

14. The apparatus of claim 13, wherein the at least one transducer includes a plurality of transducers and the program code causes the processor to apply the ultrasound signal in an alternating pattern and pulsed fashion.

15. The apparatus of claim 14, wherein the at least one transducer comprises a first transducer and a second transducer and the program code causes the processor to:
apply a first pulse of ultrasound during a first On-time period with the first transducer; and
apply a second pulse of ultrasound during a second On-time period with the second transducer, the second On-time period being outside of the first On-time period.

16. The apparatus of claim 15, wherein the program code causes the processor to:
receive a first feedback acoustic response signal from the first transducer during the second On-time period; and
receive a second feedback acoustic response signal from the second transducer during the first On-time period.

17. The apparatus of claim 13, wherein the at least one transducer includes two ultrasound transducer elements that are configured to transmit the ultrasound to a patient's skull, and the program code causes the processor to diagnose at least one of presence of a stroke, presence of the hemorrhagic stroke and presence of the ischemic stroke based at least in part on the relationship between the acoustic response signature and the baseline acoustic response signature.

18. The apparatus of claim 17, wherein, the at least one transducer comprises two transducers and the baseline acoustic response signature comprises at least one of a known normal acoustic response signature, and an acoustic response signature corresponding to an unaffected hemisphere, wherein the baseline acoustic response signature is obtained from one of the two transducers.

* * * * *